United States Patent
So et al.

(10) Patent No.: US 9,724,065 B2
(45) Date of Patent: Aug. 8, 2017

(54) MAMMOGRAPHY APPARATUS

(71) Applicant: Samsung Electronics Co., Ltd., Suwon-si (KR)

(72) Inventors: Yong Ho So, Suwon-si (KR); Dae Soo Kim, Yongin-si (KR); Young Jun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/735,521

(22) Filed: Jun. 10, 2015

(65) Prior Publication Data
US 2016/0135771 A1 May 19, 2016

(30) Foreign Application Priority Data
Nov. 14, 2014 (KR) .................. 10-2014-0158853

(51) Int. Cl.
*A61B 6/00* (2006.01)
*A61B 6/10* (2006.01)
*A61B 6/04* (2006.01)

(52) U.S. Cl.
CPC ............ *A61B 6/502* (2013.01); *A61B 6/0414* (2013.01); *A61B 6/105* (2013.01); *A61B 6/4435* (2013.01)

(58) Field of Classification Search
USPC ........................................................ 378/208
See application file for complete search history.

*Primary Examiner* — Phillip A Johnston
(74) *Attorney, Agent, or Firm* — Staas & Halsey LLP

(57) ABSTRACT

Provided is a mammography apparatus that prevents a main body from falling due to damage to a coupling connecting a ball screw, to which the main body is connected, and a motor. The mammography apparatus includes: a main body having an X-ray generator and an X-ray detector; a ball screw to which the main body is connected so as to be movable up and down; a motor rotating the ball screw so as to allow the main body to move up and down; a coupling connecting a drive shaft of the motor and the ball screw; and a brake provided at one side of the coupling. When the coupling is ruptured, the brake prevents ruptured coupling portions from being separately rotated in order to prevent a fall of the main body.

26 Claims, 16 Drawing Sheets

MAMMOGRAPHY APPARATUS

CROSS-REFERENCE TO RELATED APPLICATIONS

This application claims the benefit of Korean Patent Application No. 10-2014-0158853, filed on Nov. 14, 2014 in the Korean Intellectual Property Office, the disclosure of which is incorporated herein by reference.

BACKGROUND

1. Field

Embodiments discussed herein relate to a mammography apparatus whose main body is prevented from falling.

2. Description of the Related Art

X-ray imaging apparatuses obtain an image of an inner portion of an object using X-rays. The X-ray imaging apparatuses may visualize the inner portion of the object in a noninvasive manner by irradiating the object with X-rays and detecting the X-rays transmitted through the object. Medical X-ray imaging apparatuses may be used to diagnose an injury or a disease at the inner portion of the object which cannot be apparently or easily checked.

A mammography apparatus is one of the X-ray imaging apparatuses that can capture an image of the breast of a woman using X-rays. A doctor examines the captured image to be able to diagnose a possibility of an outbreak of breast cancer.

The mammography apparatus presses biological tissue in the breast, and then irradiates the breast with X-rays to obtain an image. A main body of the mammography apparatus may include a pressing paddle capable of pressing the breast, and an X-ray detector. The main body may be provided with a stand so as to be movable up and down.

The main body is mounted to a ball nut, and the ball nut is mounted to a ball screw. The ball nut is provided to move up and down by rotation of the ball screw, and thereby the main body can be moved up and down. The ball screw and a drive shaft connected to a motor may be connected by a coupling. The ball screw is rotated along with the drive shaft so as to be able to raise or lower the main body.

If the coupling ruptures or suddenly breaks the main body may fall and have undesirable consequences. What is needed is a mechanism that resolves this problem.

SUMMARY

Additional aspects and/or advantages will be set forth in part in the description which follows and, in part, will be apparent from the description, or may be learned by practice of the embodiments.

According to embodiments discussed herein, there is provided a mammography apparatus, which prevents a main body from falling due to damage to a coupling that connects a motor and a ball screw to which the main body is connected.

A mammography apparatus according to an embodiment includes: a main body having an X-ray generator and an X-ray detector; a ball screw to which the main body is connected so as to be movable up and down; a motor configured to rotate the ball screw so as to allow the main body to move up and down; a coupling configured to connect a drive shaft of the motor and the ball screw; and a brake provided at one side of the coupling, wherein, when the coupling is ruptured, the brake prevents ruptured coupling portions from being separately rotated in order to prevent a fall of the main body.

The brake device may include a top holder located at an upper portion of the coupling, and a bottom holder located at a lower portion of the coupling.

A stopper may be provided for the top holder, and the bottom holder may include a push bar pressing the stopper when the coupling is ruptured.

When the stopper is pressed by the push bar, the stopper may protrude from one side of the top holder.

An interfering bracket that interferes with the stopper protruding from one side of the top holder may be located at one side of the coupling.

When the stopper interferes with the interfering bracket, the ruptured coupling portions may be rotated together.

The interfering bracket may include a switch pressed by the stopper.

When the switch is pressed, a signal indicating that the coupling is ruptured may be sent to a controller.

The top holder may further include an elastic member, and the elastic member may press the stopper toward the push bar.

Further, an elastic member receiver configured to receive the elastic member may be provided in an inner portion of the stopper.

A stopper receiver may be provided at one side of the top holder.

A lateral hole may be formed in the top holder, and the stopper may protrude through the lateral hole.

A pin may be located in the lateral hole so as to cross the lateral hole.

The stopper may include a first surface and a second surface that are spaced apart from each other. When the stopper is pressed by the push bar, the pin may be positioned between the first surface and the second surface.

The bottom holder and the push bar may be provided integrally.

A mammography apparatus according to another embodiment includes: a main body having an X-ray generator and an X-ray detector; a ball screw to which the main body is connected so as to be movable up and down; a motor configured to rotate the ball screw so as to allow the main body to move up and down; a coupling configured to connect a drive shaft of the motor and the ball screw; and a brake provided at one side of the coupling, wherein the brake device includes: a top holder connected to the ball screw; a bottom holder connected to the drive shaft; and a stopper configured to restrain the top holder and the bottom holder when the coupling is ruptured.

Here, a stopper receiver configured to receive the stopper may be provided at one side of the top holder.

When the coupling is in a normal state, one side of the stopper may be supported by one side of the bottom holder.

An interfering hole into which a part of the stopper is inserted when the coupling is ruptured may be provided at one side of the bottom holder.

An elastic member may be further provided for the stopper receiver.

The elastic member may press the stopper toward the bottom holder.

A mammography apparatus according to yet another embodiment includes: a ball screw to which a main body is connected so as to be movable up and down; a motor configured to transmit a rotational force to the ball screw; a coupling, at one side of which the ball screw is connected and at the other side of which the drive shaft of the motor is connected; and a brake provided at the one side of the coupling, wherein the brake device includes, a top holder provided at the one side of the coupling and provided with a stopper, and a bottom holder provided at the other side of the coupling, and, when the coupling is ruptured, the one side of the coupling is prevented from being rotated separately from the other side of the coupling by the stopper.

Here, an interfering bracket may be provided at the one side of the coupling, and the stopper may interfere with the interfering bracket.

When the stopper interferes with the interfering bracket, the ball screw may come to a stop.

A stopper receiver configured to receive the stopper may be provided for the bottom holder.

When a part of the stopper may be inserted into the stopper receiver, the top holder and the bottom holder may be mutually restrained and rotated together.

A driving force of the motor may be transmitted to the ball screw.

According to the embodiments, a brake for preventing the main body from falling is mechanically provided, and thereby a manufacturing cost can be reduced compared to an electronic brake. The mechanical brake is stable compared to the electronic brake, because the main body is prevented from falling even when an electrical problem occurs. In addition, the brake may be applied to not only the mammography apparatus, but also other apparatuses having a similar lifting structure.

The brake may comprise a mechanical brake.

According to embodiments discussed herein a mammography apparatus may include: a main body having an x-ray generator and an x-ray detector; an arm connected to the main body; a screw to position the arm; a coupling to engage the screw; and a stop mechanism to stop the screw from changing position if the coupling breaks.

The coupling may include first and second parts and the stop mechanism may include: a bracket associated with the coupling; a push bar of the second part; and a stop rod of the second part pushed by the push bar when the first part rotates differently than the second part where the stop rod is pushed out to be in contact with the bracket to stop rotation of the second part.

The apparatus may further include a switch, activated by the stop rod when pushed out, to signal a broken coupling.

According to embodiments discussed herein a mammography apparatus may include a main body having an x-ray generator and an x-ray detector; an arm connected to the main body; a linear actuator to position the arm; and a stop mechanism to engage the linear actuator to stop the arm from changing position if the actuator breaks. The linear actuator may be a mechanical linear actuator and the stop mechanism may be a mechanical brake including an extensible phi on an arm lifting shaft that contacts a rigid bracket to stop shaft rotation.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION

Hereinafter, a mammography apparatus will be described in detail with reference to the accompanying drawings.

Figure 1:
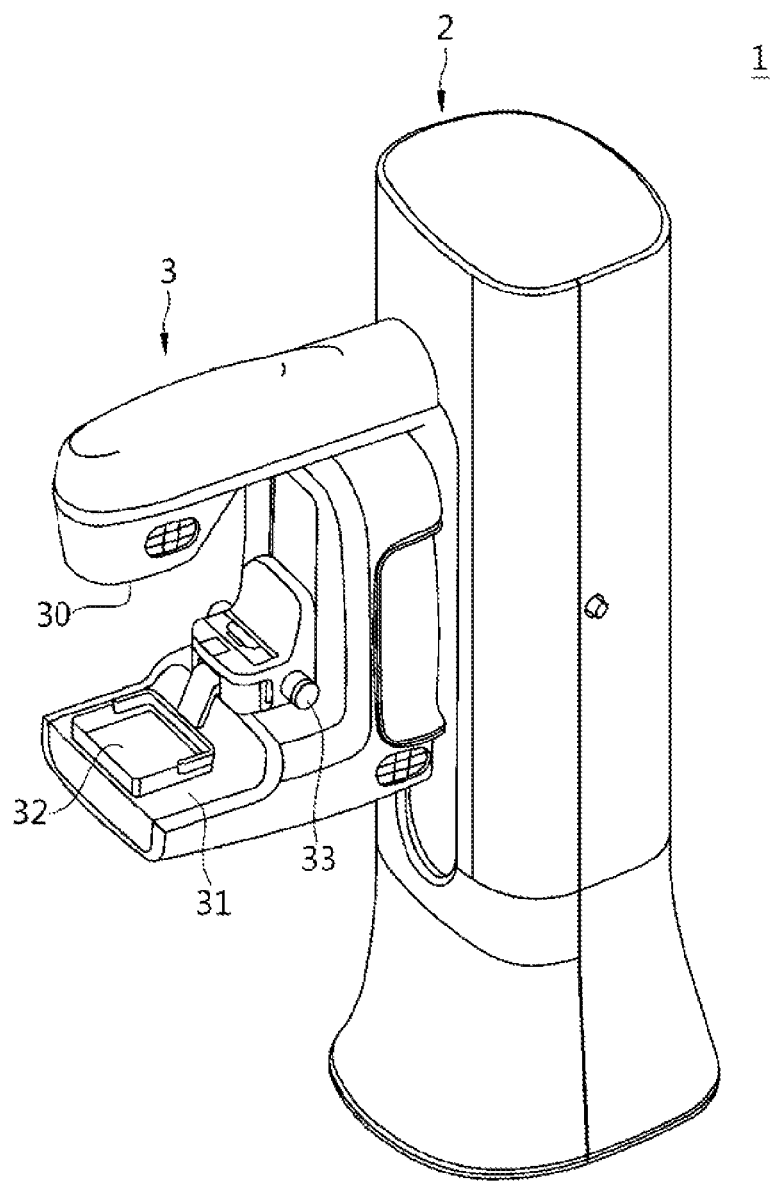
FIG. 1 is a view illustrating a mammography apparatus according to an embodiment.

FIG. 1 is a view illustrating a mammography apparatus according to an embodiment.

Referring to FIG. 1, a mammography apparatus 1 according to an embodiment includes a stand 2, and a main body 3 connected to the stand 2 so as to be movable up and down. A lesion of an object is radiographed by the main body 3.

The mammography apparatus 1 according to the embodiment is an X-ray imaging apparatus that obtains an image of an inner portion of a breast using X-rays. Hereafter, the breast may be referred to as the object for the X-ray imaging apparatus 1.

The main body 3 may include an X-ray generator 30 and an X-ray detector 31. The X-ray generator 30 and the X-ray detector 31 may be provided to face each other. The X-ray generator 30 may be located at an upper portion of the main body 3, and the X-ray detector 31 may be located at a lower portion of the main body 3.

The X-ray generator 30 generates X-rays to apply them to the object. The X-rays transmitted through the object may be detected by the X-ray detector 31. The X-ray detector 31 may convert the detected X-rays into electric signals, obtain X-ray data from the converted electric signals, and send the X-ray data to a controller.

When the object is the breast made up of soft tissue only, vertical compression is needed to obtain a more clear and accurate image. Accordingly, a pressing paddle 32 may be provided to be able to compress the object. The pressing paddle 32 may be disposed between the X-ray generator 30 and the X-ray detector 31. The object may be irradiated with the X-rays in a state in which it is disposed between the pressing paddle 32 and the X-ray detector 31 and is pressed by the pressing paddle 32.

The pressing paddle 32 may be raised or lowered vertically by a handle 33. An operator vertically moves the pressing paddle 32 so as to allow the pressing paddle 32 to be pressed under appropriate pressure. When the object is irradiated with the X-rays generated from the X-ray generator 30 with the object pressed under appropriate pressure, the X-rays transmitted through the object may be detected by the X-ray detector 31, and the X-ray data obtained by the X-ray detector 31 may be sent to the controller.

Figure 2:
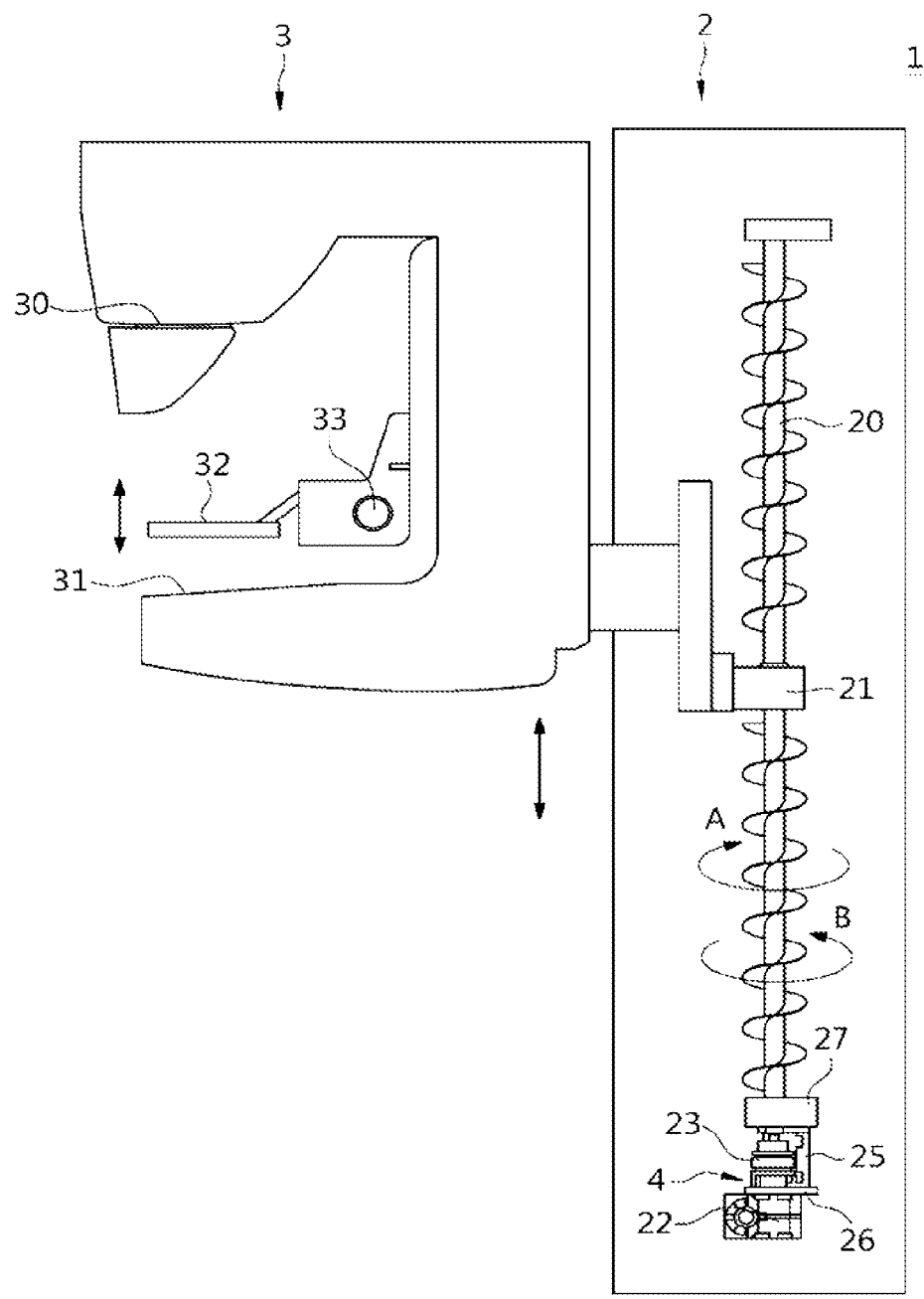
FIG. 2 is a view illustrating a lifting structure of the mammography apparatus according to the embodiment.

FIG. 2 is a view illustrating a lifting or positioning structure of the mammography apparatus according to the embodiment.

Referring to FIG. 2, the stand 2 of the mammography apparatus 1 according to one embodiment may be provided with a lifting structure configured to raise/lower the main body 3. The operator may move the main body 3 in an upward/downward direction so as to facilitate X-ray imaging depending on a position of the object.

The lifting structure of the main body 3 includes a lifting arm and a ball nut 21. The lifting arm may be a ball screw 20. The ball nut 21 may be mounted to the ball screw 20. When the ball screw 20 rotates in a clockwise or counterclockwise direction, the ball nut 21 can move up or down along the ball screw 20. The screw 20 and ball nut 21 may be a mechanical linear actuator.

The ball screw 20 may be provided for the stand 2. The ball nut 21 moved up or down by the rotation of the ball screw 20 may be mounted to the ball screw 20. The main body 3 is mounted to the ball nut 21 so as to be able to move up or down (change position) depending on a rotational direction of the ball screw 20.

Figure 3:
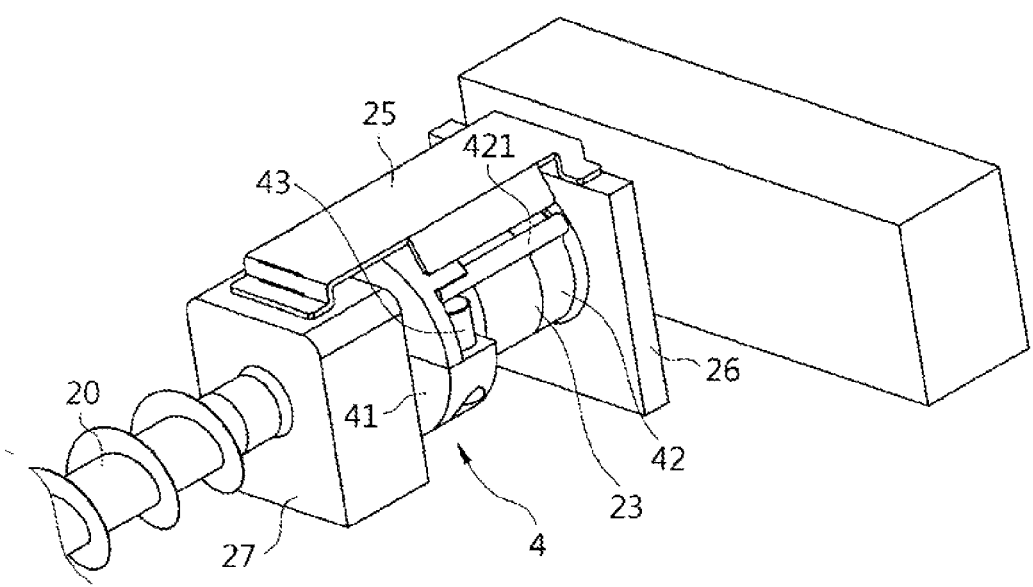
FIG. 3 is a view illustrating a part of the lifting structure of the mammography apparatus according to the embodiment.

The ball screw 20 may be rotated by a driving force transmitted from a motor 22 (see FIG. 3). When the ball screw 20 is rotated in place by the driving force of the motor 22, the ball nut 21 may move up or down along the ball screw 20. The main body 3 connected to the ball nut 21 may move up or down together with the ball nut 21. The ball nut 21 and ball screw 20 may be considered a traveling-nut type of linear actuator.

Hereinafter, a description will be made of an embodiment in which, when the ball screw 20 rotates in a clockwise direction A, the ball nut 21 moves up, and when the ball screw 20 rotates in a counterclockwise direction B, the ball nut 21 moves down. Of course, the opposite motion can be obtained by revising the threads of the screw 20 and nut 21.

The ball screw 20 is provided with a coupling 23 at one side thereof which connects the motor 22 and the ball screw 20. The ball screw 20 may be provided with a mechanical brake 4 capable of preventing the main body 3 from falling due to damage to the coupling 33. A transmission structure configured to transmit power to the ball screw 20 and a structure of the brake 4 will be described below.

Figure 4:
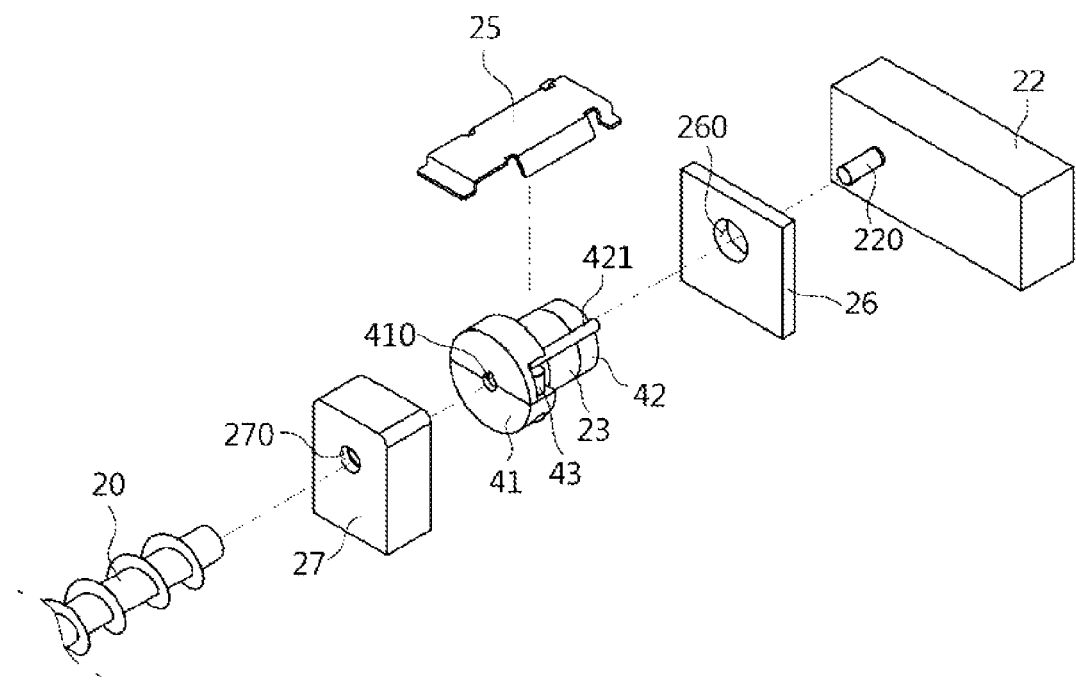
FIG. 4 is an exploded perspective view illustrating a part of the lifting structure of the mammography apparatus according to the embodiment.

FIG. 3 is a view illustrating a part of the lifting structure of the mammography apparatus according to the embodiment, and FIG. 4 is an exploded perspective view illustrating a part of the lifting structure of the mammography apparatus according to the embodiment.

Referring to FIGS. 3 and 4, the ball screw 20 of the mammography apparatus 1 according to the embodiment may be rotated by the driving force transmitted from the motor 22. The ball screw 20 may be connected to the motor 22 by the coupling 23. The ball screw 20 may be connected to one side of the coupling 23. A drive shaft 220 connected to the motor 22 may be connected to the other side of the coupling 23.

The driving force of the motor 22 may be transmitted to the ball screw 20 via the drive shaft 220 and the coupling 23, so that the ball screw 20 can be rotated in the clockwise or counterclockwise direction. When the drive shaft 220 is rotated in one direction by the motor 22, the coupling 23 and the ball screw 20 can also be rotated in one direction together with the drive shaft 220.

The ball screw 20 may be provided with the brake 4. The brake 4 may be provided to prevent the main body 3 from falling due to damage to the coupling 23.

When the coupling 23 is in a normal state, the coupling 23 and the ball screw 20 may be rotated at the same speed and in the same rotational direction as the drive shaft 220 by the driving force of the motor 22. When the drive shaft 220 is rotated in the clockwise direction A, the coupling 23 and the ball screw 20 may be rotated at the same speed as the drive shaft 220 in the clockwise direction A. Here, the ball nut 21 can be raised by the ball screw 20.

As an example, when a rupture or sudden breaking of the coupling 23 occurs while the drive shaft 220 is rotated in the clockwise direction A, upper and lower portions of the coupling 23 may be rotated in different directions. When the coupling 23 is ruptured into upper and lower couplings while the drive shaft 220 is rotated in the clockwise direction A, the lower coupling to which the drive shaft 220 is connected continues to be rotated in the clockwise direction A together with the drive shaft 220, while a rotational force of the lower coupling is not transmitted to the upper coupling.

At this time, the ball screw 20 may be rotated by the weight of the main body 3 connected thereto in a direction in which the main body 3 attempts to move downward. The ball screw 20 and the upper coupling to which the ball screw 20 is connected may be rotated in the counterclockwise direction B in which the main body 3 moves downward. The ball screw 20 does not receive the driving force of the motor 22, and thus is rotated in the counterclockwise direction B, so that the main body 3 can fall.

When the rupture of the coupling 23 occurs while the drive shaft 220 is rotated in the counterclockwise direction B, a difference between the rotational speeds of the upper and lower portions of the coupling 23 may occur. The lower coupling is rotated together with the drive shaft 220, and a rotating force of the drive shaft 220 is not transmitted to the upper coupling. The ball screw 20 and the upper coupling may be rotated faster than the drive shaft 220 due to the weight of the main body 3 connected to the ball screw 20, and the main body 3 may fall at a high speed.

In order to prevent the main body 3 from falling due to the rupture of the coupling 23, the ball screw 20 may be provided with the brake 4 which is configured to prevent the ball screw 20 from being further rotated when the coupling 23 is ruptured. The rotation of the ball screw 20 is prevented by the brake 4 regardless of the driving force. Thereby, the main body 3 can be prevented from falling.

A bracket 26 to which the motor 22 may be mounted is provided at one side of the coupling 23. As an example, the bracket 26 may be provided under the coupling 23. The coupling 23 may be mounted to one face of the bracket 26, and the motor 22 may be mounted to the other face of the bracket 26. A hole 260 through which the drive shaft 220 passes may be formed in the bracket 26. The drive shaft 220 may pass through the hole 260, and be connected to the coupling 23.

A support 27 may be provided at the other side of the coupling 23. The support 27 may be provided on the coupling 23. A hole 270 through which the ball screw 20 may pass may be formed in the support 27. The support 27 may be mounted to the ball screw 20 and cover the upper portion of the coupling 23.

An interfering bracket 25 may be provided radially outside of the coupling 23. The interfering bracket 25 may be mounted to at least one of the bracket 26 and the support 27 that are provided below and above the coupling 23, respectively. The interfering bracket 25 may be located radially outside of the coupling 23, and may interfere with a stopper 43 (see FIG. 6) which protrudes from the brake 4 when the coupling 23 is ruptured. A position at which the interfering bracket 25 is mounted is not limited by that described above, but the interfering bracket 25 may be provided at any position as long as it can interfere with the protruding stopper 43 when the coupling 23 is ruptured.

Figure 5:
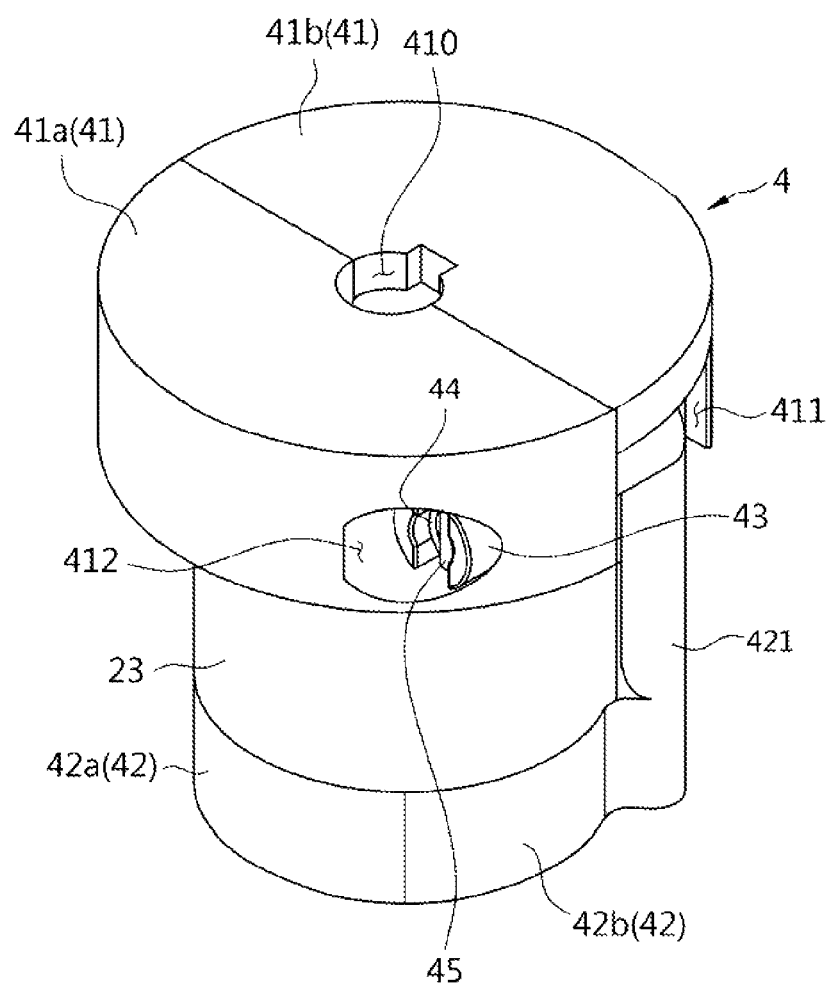
FIG. 5 is a view illustrating a brake and a coupling according to an embodiment.
Figure 6:
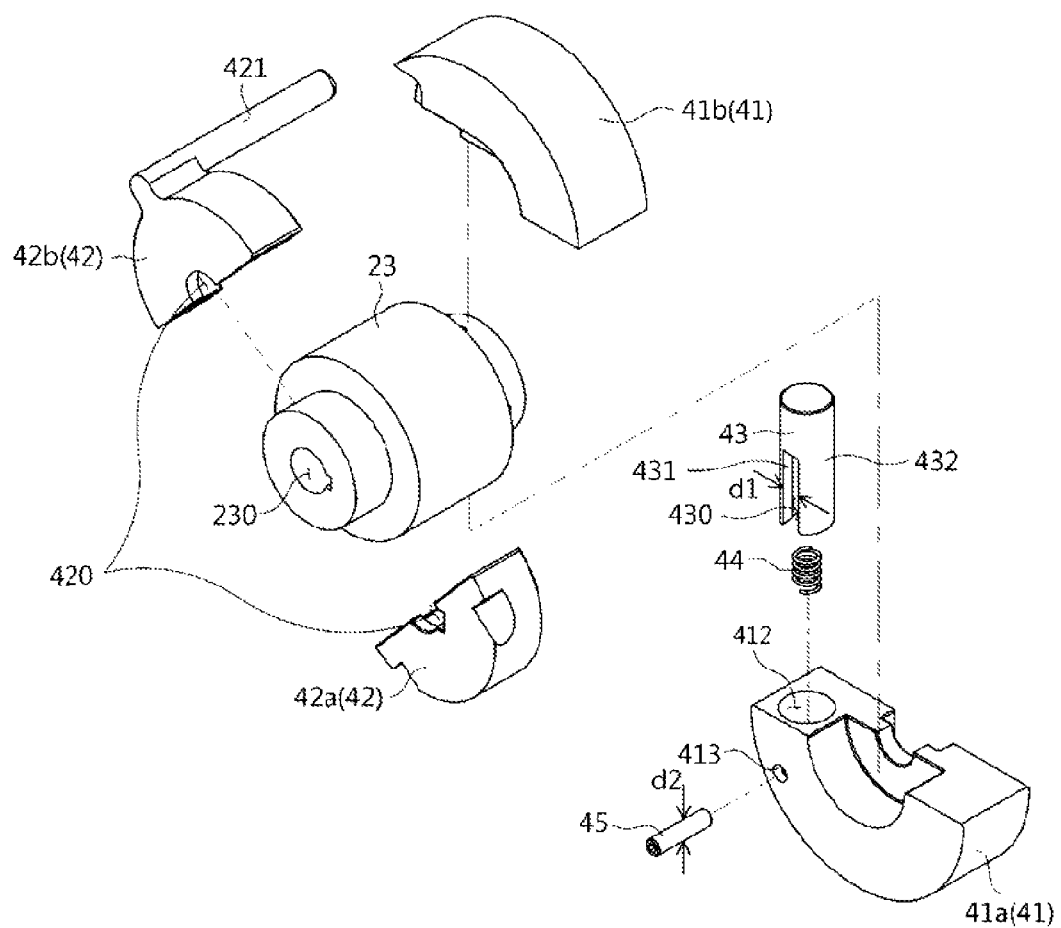
FIG. 6 is an exploded perspective view illustrating the brake and the coupling according to the embodiment.

FIG. 5 is a view illustrating a brake and a coupling according to an embodiment, and FIG. 6 is an exploded perspective view illustrating the brake and the coupling according to the embodiment.

Referring to FIGS. 5 and 6, the brake 4 according to the embodiment may include a top holder 41 and a bottom holder 42. The top holder 41 may be located at the upper portion of the coupling 23, and the bottom holder 42 may be located at the lower portion of the coupling 23.

The top holder 41 may be provided with a hole 410 through which the ball screw 20 may pass. A protrusion or shaft key may be formed at one side of the ball screw 20 which passes through the hole 410 formed in the top holder 41. The hole 410 formed in the top holder 41 may be provided to have a shape (a key way) which corresponds to an outer surface (the shaft key) of the ball screw 20 from which the protrusion is formed. The protrusion formed from the ball screw 20 is inserted into the hole 410 and interfere with the hole 410, and thereby the ball screw 20 and the top holder 41 can be rotated together.

The top holder 41 may be provided with a stopper receiver 411 into which the stopper 43 is inserted. The stopper receiver 411 may be provided at a lower side of the top holder 41. A sidewall of the top holder 41 at which the stopper receiver 411 is located may be partly opened.

A lateral hole 412 may be provided in the sidewall of the top holder 41, and the stopper 43 received in the stopper receiver 411 may protrude through the lateral hole 412. The lateral hole 412 may communicate with the stopper receiver 411. The stopper 43 may protrude outside the top holder 41 through the lateral hole 412 when the coupling 23 is ruptured.

An elastic member receiver 430 into which an elastic member 44 may be inserted may be provided in an inner portion of the stopper 43. The stopper 43 may include a first surface 431 and a second surface 432 which are spaced apart from each other by a given distance d1. The distance d1 between the first surface 431 and the second surface 432 may be equal to or somewhat greater than a diameter d2 of a pin 45. The elastic member receiver 430 may be provided between the first surface 431 and the second surface 432.

A pin mounting portion 413 into which the pin 45 may be inserted may be provided in an upper or lower surface of the top holder 41. The pin 45 inserted into the pin mounting portion 413 may be located to cross the lateral hole 412 formed in the sidewall of the top holder 41.

The bottom holder 42 may be provided with a hole 420 into which the drive shaft 220 connected to the motor 22 may be inserted. Similar to the hole 410 formed in the top holder 41, a protrusion may be provided on the outer surface of the drive shaft 220, and the hole 420 formed in the bottom holder 42 may be provided to correspond to a shape of the outer surface of the drive shaft 220 from which the protrusion is formed. The protrusion formed from the drive shaft 220 may be inserted into the hole 420 and interfere with the hole 420. Thereby, the drive shaft 220 and the bottom holder 42 can be rotated together.

The bottom holder 42 may be provided with a push bar 421. The push bar 421 may extend perpendicular to a lower surface of the bottom holder 42. A part of the push bar 421 may be inserted into the stopper receiver 411 provided for the top holder 41. The push bar 421 may press the stopper 43 when the coupling 23 is ruptured. The pressed stopper 43 may protrude outside the top holder 41 through the lateral hole 412.

The top holder 41 may include a first top holder 41a that covers a part of an upper surface of the coupling 23, and a second top holder 41b that covers the other part of the upper surface of the coupling 23. The first top holder 41a and the second top holder 41b may be coupled by a fastening member. The stopper receiver 411 may be provided in such a manner that the sidewall of any one of the first top holder 41a and the second top holder 41b is partly cut out. The lateral hole 412 through which the stopper 43 may protrude may be provided in the other of the first top holder 41a and the second top holder 41b.

Similarly, the bottom holder 42 may include a first bottom holder 42a which covers a part of a lower surface of the coupling 23, and a second bottom holder 42b which covers the other part of the lower surface of the coupling 23. The first bottom holder 42a and the second bottom holder 42b may be coupled by a fastening member.

The top holder 41 and the bottom holder 42 may be each provided in one body.

The elastic member 44 may be received in the elastic receiver 430 of the stopper 43. The stopper 43 in which the elastic member 44 is received may be received in the stopper receiver 411 provided for the top holder 41. The pin 45 may be inserted into the pin mounting portion 413 provided in the top holder 41, and be located to extend vertically. The stopper 43 may extend perpendicular to an extending direction of the ball screw 20. End portions of the first and second surfaces 431 and 432 of the stopper 43 may be located to be directed to the lateral hole 412. When the coupling 23 is ruptured, and when the stopper 43 is pressed by the push bar 421 and protrudes through the lateral hole 412, the pin 45 may be inserted between the first surface 431 and the second surface 432.

The stopper 43 and the elastic member 44 may not be separated from the stopper receiver 411 by the pin 45. The pin 45 may press the elastic member 44 received in the stopper 43, and the elastic member 44 may press one side of an inner portion of the stopper 43 which forms the elastic member receiver 430. The stopper 43 may be pushed in a direction in which the stopper 43 moves away from the pin 45 by an elastic force of the elastic member 44. At this time, one side of the stopper 43 may be in contact with the push bar 421.

At least a part of the push bar 421 may be inserted into the elastic member receiver 430. The push bar 421 may be located at one side of the stopper 43. When the coupling 23 is in a normal state, the push bar 421 is located at the one side of the stopper 43, and may be in contact with the stopper 43. At this time, the stopper 43 may press a lateral portion of the push bar 421 by an elastic force of the elastic member 44. When the coupling 23 is ruptured, the push bar 421 is provided to allow the one side of the stopper 43 to be pressed by a force greater than the elastic force from the elastic member 44.

Figure 7:
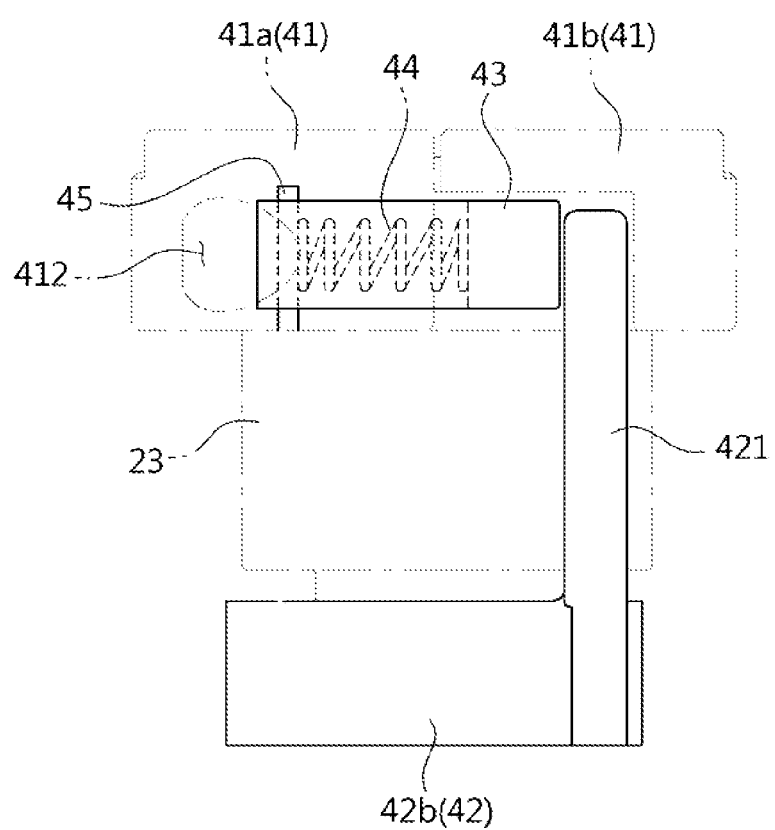
FIG. 7 is a view illustrating the brake according to the embodiment when the coupling is in a normal state.

FIG. 7 is a view illustrating the brake according to the embodiment when the coupling is in a normal state.

Referring to FIG. 7, when the coupling 23 according to the embodiment is in a normal state, the stopper 43 of the brake 4 does not protrude from the top holder 41. The elastic member 44 received in the stopper 43 may be pressed, and one side of the stopper 43 may be brought into contact with the push bar 421 by the elastic force of the elastic member 44.

The driving force of the motor 22 may be transmitted to the ball screw 20 via the drive shaft 220 and the coupling 23. The ball screw 20 connected to the side of the top holder 41 may be rotated at the same speed and in the same rotational direction as the drive shaft 220 connected to the bottom holder 42.

That is, when the coupling 23 is in the normal state, the ball screw 20 may be rotated at the same speed and in the same rotational direction as the drive shaft 220 with one side of the stopper 43 kept in contact with the push bar 421. The main body 3 may be moved up or down depending on the rotational direction of the ball screw 20.

As an example, when the drive shaft 220 and the ball screw 20 are rotated in the clockwise direction A, the main body 3 may be raised, and when the drive shaft 220 and the ball screw 20 are rotated in the counterclockwise direction B, the main body 3 may be lowered.

When the coupling 23 is ruptured, the rotational speed and direction of the side of the top holder 41 may be different from those of the side of the bottom holder 42. Hereinafter, a description will be made of a structure in which the rotation of the ball screw 20 is stopped by the brake 4 when the coupling 23 is ruptured.

Figure 8:
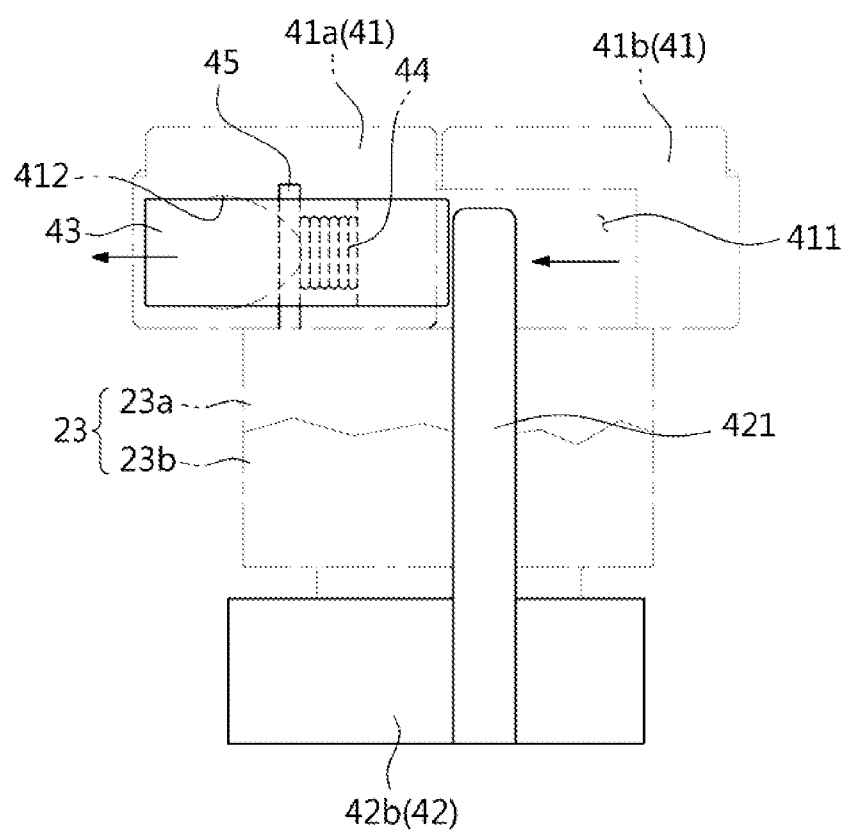
FIG. 8 is a view illustrating the brake according to the embodiment when the coupling is damaged.
Figure 9:
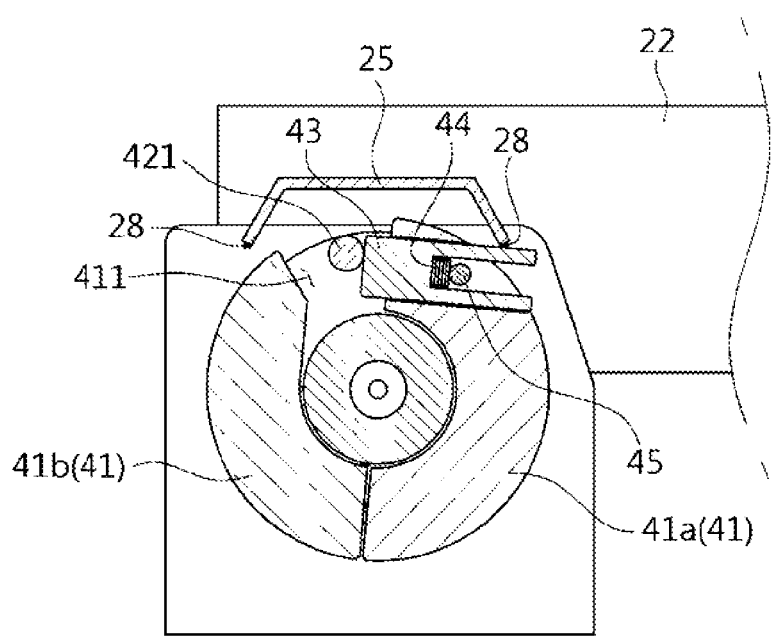
FIG. 9 is a view illustrating a state in which a switch is provided for the brake according to the embodiment.

FIG. 8 is a view illustrating the brake according to the embodiment when the coupling is damaged, and FIG. 9 is a view illustrating a state in which a switch is provided for the brake according to the embodiment.

Referring to FIGS. 8 and 9, when the coupling 23 according to the embodiment is ruptured into the upper coupling 23a and the lower coupling 23b, a difference in the rotational direction or speed between the ball screw 20 connected to the upper coupling 23a and the drive shaft 220 connected to the lower coupling 23b may occur.

As an example, when the coupling 23 is ruptured while the main body 3 is raised by the rotation of the drive shaft 220 and the ball screw 20 in the clockwise direction A, the side of the upper coupling 23a and the side of the lower coupling 23b may be rotated in different directions. The drive shaft 220 connected to the side of the lower coupling 23b continues to be rotated in the clockwise direction A by the driving force of the motor 22, while the rotating force of the drive shaft 220 is not transmitted to the ball screw 20 connected to the side of the upper coupling 23a. The ball screw 20 may be rotated in a direction in which the main body 3 attempts to move downward by its weight, that is, in the counterclockwise direction B.

Accordingly, the upper coupling 23a to which the ball screw 20 is connected may be rotated in the counterclockwise direction B, and the lower coupling 23b to which the drive shaft 220 is connected may be rotated in the clockwise direction A. At this time, the top holder 41 provided at the side of the upper coupling 23a may be rotated in the counterclockwise direction B, and the bottom holder 42 provided at the side of the lower coupling 23b may be rotated in the clockwise direction A.

Due to the different rotational directions of the upper coupling 23a and the lower coupling 23b, the push bar 421 provided for the bottom holder 42 may be rotated together with the bottom holder 42 in the clockwise direction A, and then press one side of the stopper 43.

The stopper 43 pressed by the push bar 421 with a force greater than the elastic force of the elastic member 44 may protrude outside the top holder 41 through the lateral hole 412 of the top holder 41. The protruding stopper 43 may interfere with the interfering bracket 25 located radially outside of the coupling 23. When the stopper 43 interferes with the interfering bracket 25, the top holder 41, the upper coupling 23a coupled with the top holder 41, and the ball screw 20 connected to the upper coupling 23a may be stopped such that they are no longer rotated.

When the coupling 23 is ruptured while the main body 3 is lowered by the rotation of the drive shaft 220 and the ball screw 20 in the counterclockwise direction B, the rotational speed of the upper coupling 23a may be different from that of the lower coupling 23b. The ball screw 20 may receive a force in a direction in which the main body 3 attempts to move downward due to its own weight, and thus may rotate faster than the rotational speed caused by the drive shaft 220 in the counterclockwise direction B. Accordingly, the upper coupling 23a to which the ball screw 20 is connected may rotate at a faster speed than the lower coupling 23b to which the drive shaft 220 is connected.

The top holder 41 provided at the side of the upper coupling 23a may rotate at a faster speed than the bottom bolder 42 provided at the side of the lower coupling 23b in the counterclockwise direction B. As the speed of the side of the bottom holder 42 is slower than that of the side of the top holder 41, the push bar 421 provided for the bottom holder 42 may press one side of the stopper 43 provided at the side of the top holder 41. The stopper 43 pressed by the push bar 421 may protrude outside the top holder 41 through the lateral hole 412. The stopper 43 protruding outside the top holder 41 may interfere with the interfering bracket 25. When the stopper 43 interferes with the interfering bracket 25, the top holder 41, the upper coupling 23a coupled with the top holder 41, and the ball screw 20 connected to the upper coupling 23a may be stopped such that they are no longer rotated.

When the coupling 23 is ruptured, the stopper 23 protruding outside the top holder 41 interferes with the interfering bracket 25, and thereby the ball screw 20 may be no longer rotated. The main body 3 can be prevented from moving downward by stopping the rotation of the ball screw 20.

The interfering bracket 25 may be provided with a switch 28 (see FIG. 9) that may be pressed by the stopper 43. The switch 28 is provided at one side of the interfering bracket 25, and may be pressed by the stopper 43 protruding from the top holder 41. When the switch 28 is pressed by the protruding stopper 43, a signal indicating that the coupling 23 is ruptured may be sent to the controller (not shown). The controller that has received the signal may stop the operation of the mammography apparatus 1.

The brake 4 according to the embodiment may prevent the ball screw 20 from being rotated by a mechanical structure, and thus prevent the main body 3 from falling. When an electronic brake is applied, an electric problem may occur, and thus the electronic brake may not work. The electronic brake is manufactured at a higher cost than the brake having the mechanical structure. The brake having the mechanical structure as in the embodiments has advantages that the manufacturing cost is low and a fall of the main body 3 can be reliably prevented.

Figure 10:
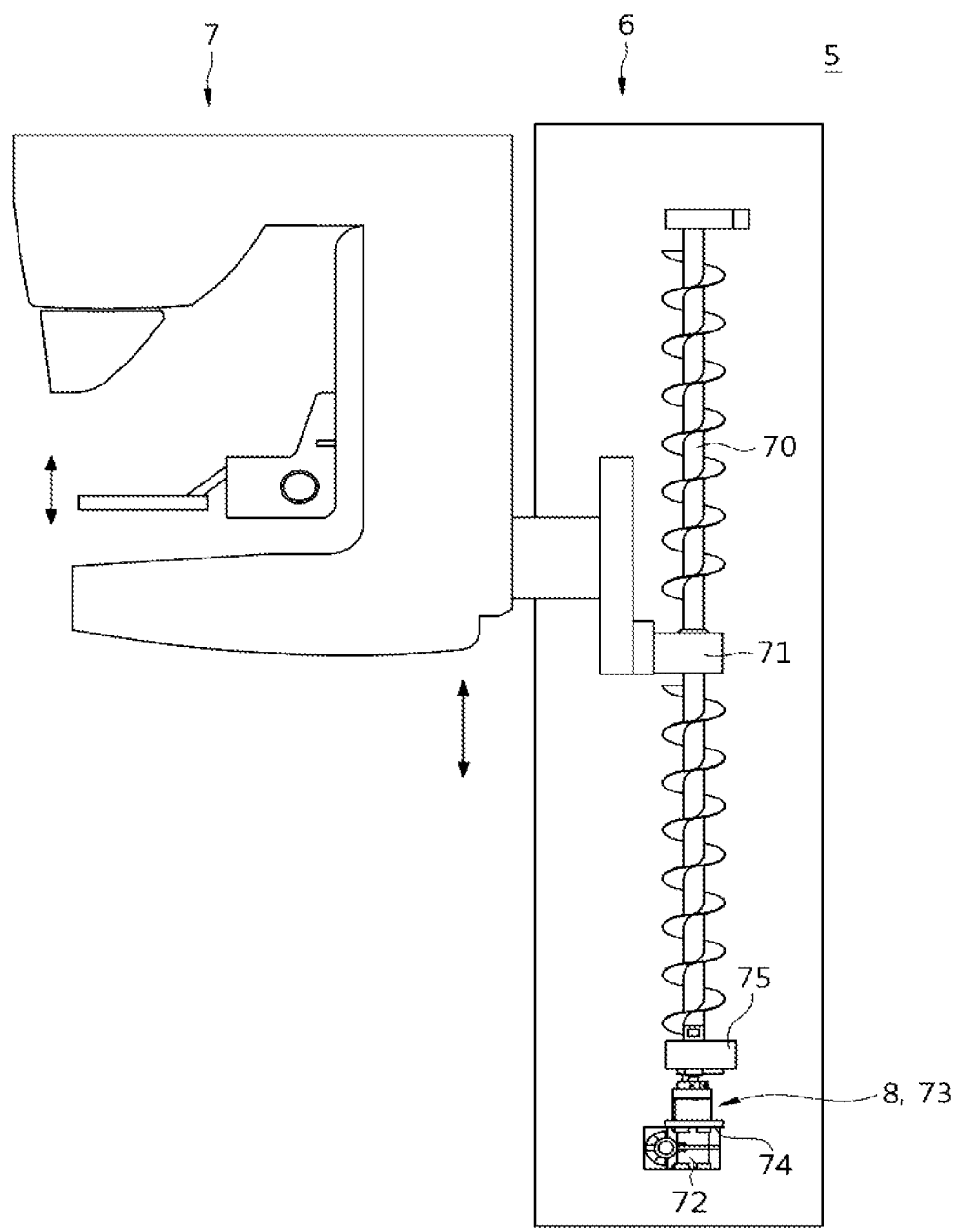
FIG. 10 is a view illustrating a lifting structure of a mammography apparatus according to another embodiment.

FIG. 10 is a view illustrating a lifting structure of a mammography apparatus according to another embodiment.

Referring to FIG. 10, a mammography apparatus 5 according to another embodiment includes a stand 6 and a main body 7 connected to the stand 2 so as to be movable up and down. The stand 6 may be provided with a lifting structure so as to raise/lower the main body 7.

The lifting structure of the main body 7 includes a ball screw 70 and a ball nut 71. The ball nut 71 is mounted to the ball screw 70. When the ball screw 70 is rotated in a clockwise direction or a counterclockwise direction, the ball nut 71 may move upward or downward along the ball screw 70.

The stand 6 may be provided with the ball screw 70. The ball screw 70 may be rotated by a driving force transmitted from a motor 72. The ball screw 70 may be provided with a coupling 73 at one side thereof which connects the motor 72 and the ball screw 70. The ball screw 70 may be provided with a brake 8 capable of preventing the main body 7 from falling when the coupling 73 is ruptured.

Figure 11:
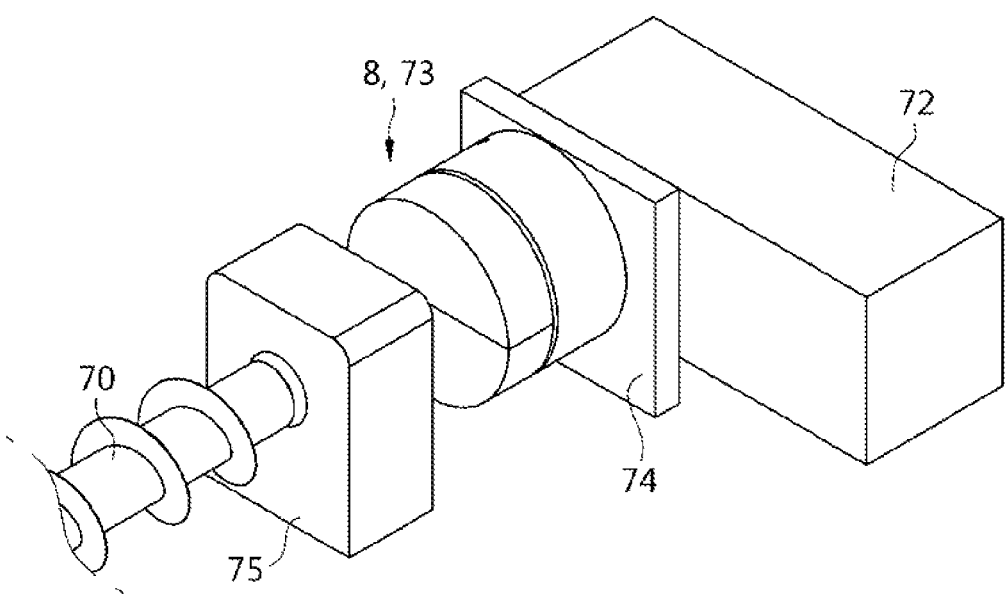
FIG. 11 is a view illustrating a part of the lifting structure of the mammography apparatus according to the other embodiment.
Figure 12:
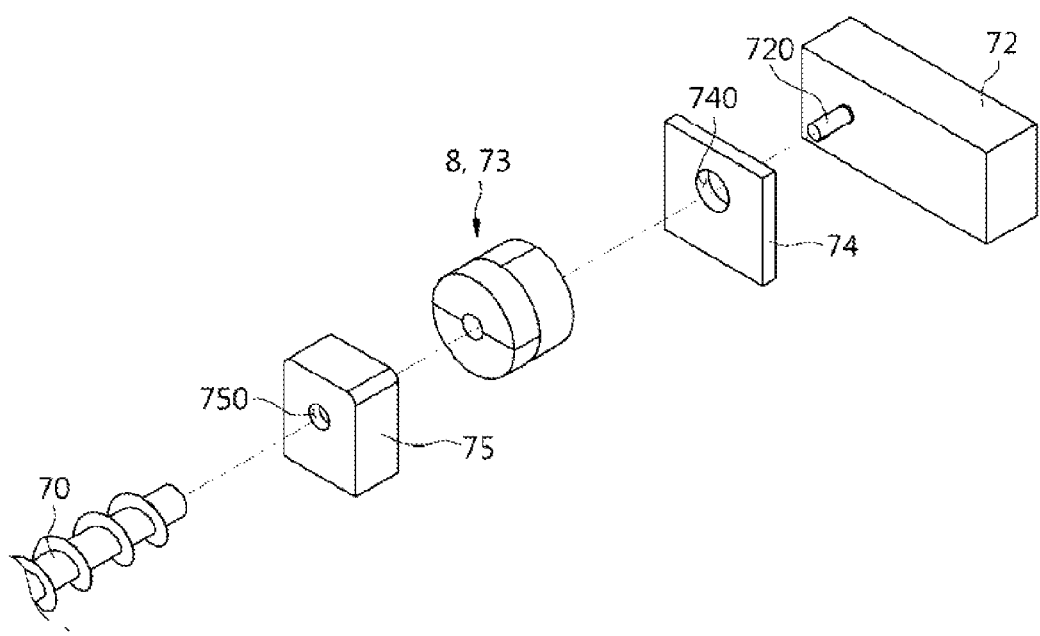
FIG. 12 is an exploded perspective view illustrating a part of the lifting structure of the mammography apparatus according to the other embodiment.

FIG. 11 is a view illustrating a part of the lifting structure of the mammography apparatus according to the other embodiment, and FIG. 12 is an exploded perspective view illustrating a part of the lifting structure of the mammography apparatus according to the other embodiment.

Referring to FIGS. 11 and 12, the ball screw 70 of the mammography apparatus 5 according to the other embodiment may be rotated by the driving force transmitted from the motor 72. The ball screw 70 may be connected to the motor 72 by the coupling 73. The ball screw 70 may be connected to one side of the coupling 73. A drive shaft 720 connected the motor 72 may be connected to the other side of the coupling 73.

The driving force of the motor 72 may be transmitted to the ball screw 70 via the drive shaft 720 and the coupling 73, and thus the ball screw 70 may be rotated in the clockwise direction or the counterclockwise direction. When the drive shaft 720 is rotated in one direction, the coupling 73 and the ball screw 70 may also be rotated in the same direction together with the drive shaft 720.

The ball screw 70 may be provided with the brake 8. The brake 8 may be provided to prevent the main body 7 from falling due to the rupture of the coupling 73.

Similar to the aforementioned embodiment, when the coupling 73 is in a normal state, the ball screw 70 and the drive shaft 720 may be rotated at the same speed and in the same rotational direction. However, when the coupling 73 is ruptured, the screw 70 and the drive shaft 720 may be rotated in different rotational directions, or at different speeds and in the same rotational direction.

Specifically, the coupling 73 is in the normal state, the coupling 73 and the ball screw 70 may be rotated at the same speed and in the same rotational direction as the drive shaft 720 by the driving force of the motor 72. When the drive shaft 720 is rotated in the clockwise direction A, the coupling 73 and the ball screw 70 may be rotated at the same speed as the drive shaft 720 in the clockwise direction A. At this time, the ball nut 71 may be raised by the ball screw 70.

When the coupling 73 is ruptured while the drive shaft 720 is rotated in the clockwise direction A, upper and lower portions of the coupling 73 may be rotated in different directions. When the coupling 73 is ruptured into an upper coupling and a lower coupling while the drive shaft 720 is rotated in the clockwise direction A, the lower coupling to which the drive shaft 720 is connected continues to be rotated together with the drive shaft 720, while a rotating force of the lower coupling may not be transmitted to the upper coupling. At this time, the ball screw 70 may be rotated by the weight of the main body 7 connected thereto in a direction in which the main body 7 attempts to move downward. The ball screw 70 and the upper coupling to which the ball screw 70 is connected may be rotated in the counterclockwise direction B in which the main body 7 moves downward. The ball screw 70 does not receive the driving force and is rotated in the counterclockwise direction B. As a result, the main body 7 may fall.

When the coupling 73 is ruptured while the drive shaft 720 is rotated in the counterclockwise direction B, a difference between the rotational speeds of the upper and lower portions of the coupling 23 may occur. The lower coupling is rotated together with the drive shaft 720, and a rotating force of the drive shaft 720 is not transmitted to the upper coupling. The ball screw 70 and the upper coupling may be rotated faster than the drive shaft 720 due to the weight of the main body 7 connected to the ball screw 70, and the main body 7 may fall at a faster speed.

In order to prevent the main body 7 from falling, the ball screw 70 may be provided with the brake 8 that restricts the rotation of the ball screw 70. The rotation of the ball screw 70 is prevented by the brake 8 regardless of the driving force, and thus the fall of the main body 7 may be prevented.

A bracket 74 to which the motor 72 may be mounted is provided at one side of the coupling 73. As an example, the bracket 76 may be provided under the coupling 73. The coupling 73 may be mounted to one face of the bracket 74, and the motor 72 may be mounted to the other face of the bracket 74. A hole 740 through which the drive shaft 720 passes may be formed in the bracket 74. The drive shaft 720 may pass through the hole 740, and be connected to the coupling 73.

A support 75 may be provided at the other side of the coupling 73. The support 75 may be provided on the coupling 73. A hole 750 into which the ball screw 70 may be inserted may be formed in the support 75. The support 75 may be mounted to the ball screw 70 and cover the upper portion of the coupling 73.

Figure 13:
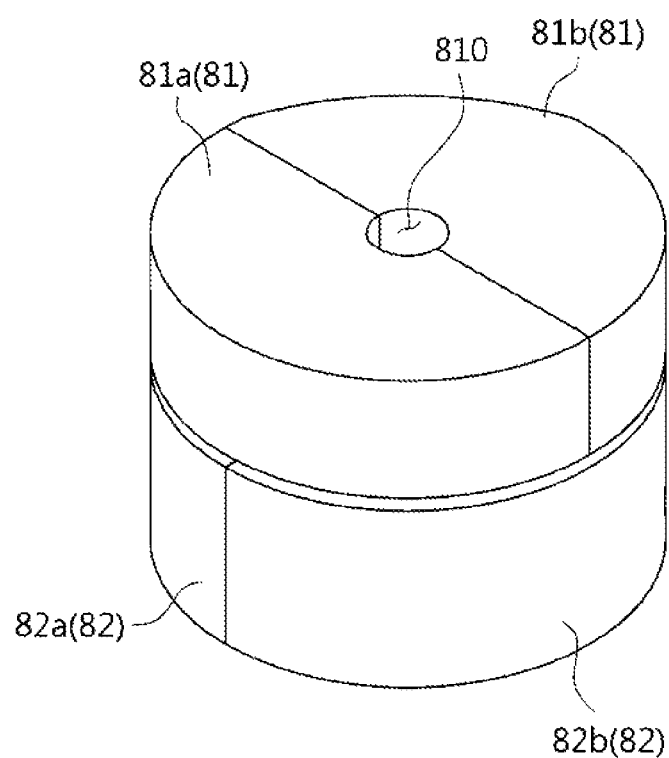
FIG. 13 is a view illustrating a brake and a coupling according to another embodiment.
Figure 14:
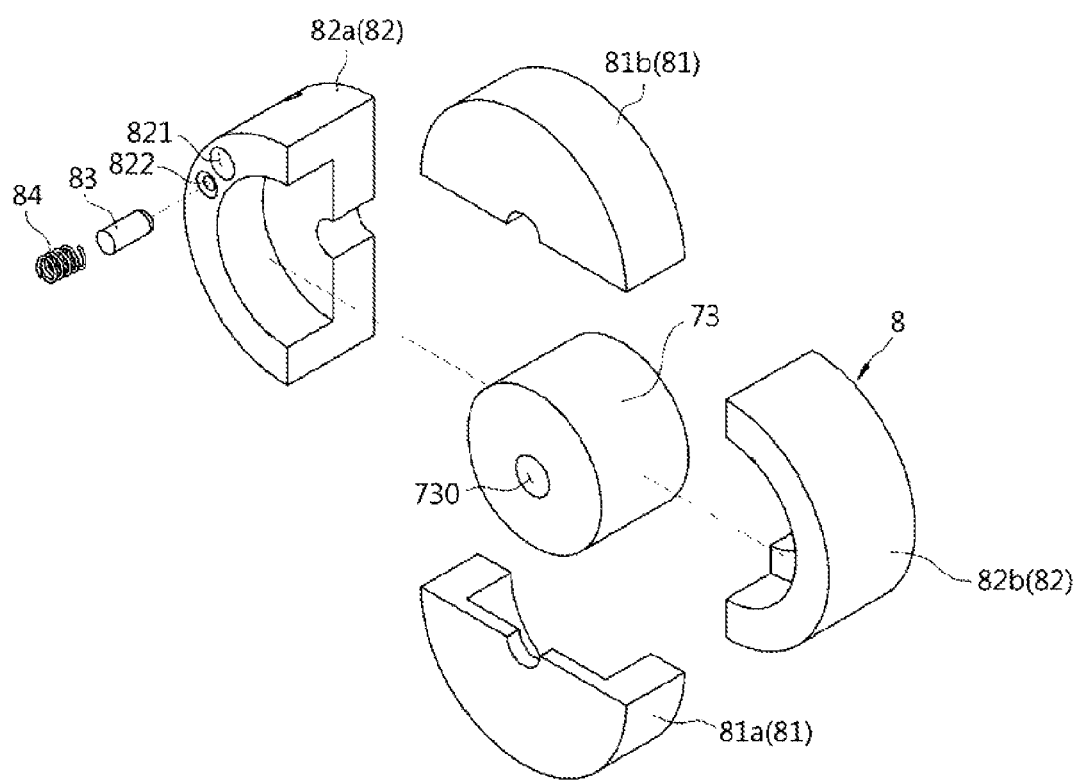
FIG. 14 is an exploded perspective view illustrating the brake and the coupling according to the other embodiment.

FIG. 13 is a view illustrating a brake and a coupling according to another embodiment, and FIG. 14 is an exploded perspective view illustrating the brake and the coupling according to the other embodiment.

Referring to FIGS. 13 and 14, the brake 8 according to the other embodiment may include a top holder 81 and a bottom holder 82. The top holder 81 may be located at the upper portion of the coupling 73, and the bottom holder 82 may be located at the lower portion of the coupling 73.

The top holder 81 may be provided with a hole 810 through which the ball screw 70 may pass. A protrusion 700 may be formed at one side of the ball screw 70 that passes through the hole 810 formed in the top holder 81. The hole 810 formed in the top holder 81 may have a shape corresponding to an outer surface of the ball screw 70 from which the protrusion 700 is formed. The protrusion 700 formed from the ball screw 70 is inserted into the hole 810 and interferes with the hole 810, thereby the ball screw 70 and the top holder 81 can be rotated together.

The top holder 81 may be provided with a stopper receiver 811. The stopper receiver 811 may be provided in a sidewall of the top holder 81. The stopper receiver 811 may be provided in the form of a hole that vertically extends from the bottom of the top holder 81. The stopper 83 may be received in the stopper receiver 811. The stopper receiver 811 may further receive an elastic member 84 that presses a stopper 83. The elastic member 84 may be received in the stopper receiver 811 so as to provide the stopper 83 with an elastic force directed toward the bottom holder 82.

The bottom holder 82 may be provided with a hole 820 to which the drive shaft 720 connected to the motor 72 may be connected. Similar to the hole 810 formed in the top holder 81, the outer surface of the drive shaft 720 may be provided with a protrusion 721, and the hole 820 formed in the bottom holder 82 may be provided to correspond to a shape of the outer surface of the drive shaft 720 from which the protrusion 721 is formed. The protrusion 721 formed from the drive shaft 720 is inserted into the hole 820 and interferes with the hole 820. Thereby, the drive shaft 720 and the bottom holder 82 can be rotated together.

An interfering hole 821 may be provided at one side of the bottom holder 82. The interfering hole 821 may be provided in an upper surface of the bottom holder 82. When the top holder 81 and the bottom holder 82 are rotated at different rotational speeds or in different rotational directions due to the rupture of the coupling 73, the stopper 83 received in the stopper receiver 811 of the top holder 81 may slide toward the interfering hole 821.

The bottom holder 82 may be provided with a stopper seat 822 in which the stopper 83 is seated. The stopper seat 822 may be provided in a shallow recess form so that the stopper 83 seated in the stopper seat 822 easily comes out of the stopper seat 822 by an external force. One side of the stopper 83 which is received in the stopper receiver 811 of the top holder 81 may be seated in the stopper seat 822, and a position of the stopper 83 may be fixed on the upper surface of the bottom holder 82. The stopper seat 822 may be provided at a position proximate to the stopper receiver 811. When the top holder 81 and the bottom holder 82 are rotated at different rotational speeds or in different rotational directions due to the rupture of the coupling 73, one side of the stopper 83 may come out of the stopper seat 822 to slide on the upper surface of the bottom holder 82, and then be inserted into the interfering groove 821.

The top holder 81 may include a first top holder 81a that covers a part of the upper surface of the coupling 73, and a second top holder 81b that covers the other part of the upper surface of the coupling 73. The first top holder 81a and the second top holder 81b may be coupled by a fastening member. The stopper receiver 811 may be provided for any one of the first top holder 81a and the second top holder 81b.

Similarly, the bottom holder 82 may include a first bottom holder 82a that covers a part of the lower surface of the coupling 73, and a second bottom holder 82b that covers the other part of the lower surface of the coupling 73. The first bottom holder 82a and the second bottom holder 82b may be coupled by a fastening member.

The top holder 81 and the bottom holder 82 may be provided in one body.

Hereinafter, an operation of the brake 8 when the coupling 73 is in a normal state or when the coupling 73 is ruptured will be described.

Figure 15:
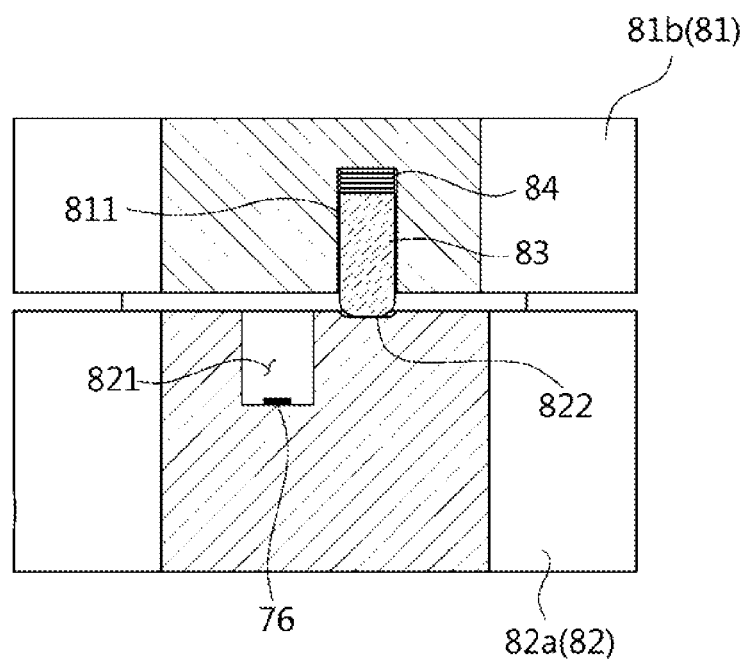
FIG. 15 is a view illustrating the brake according to the other embodiment when the coupling is in a normal state.

FIG. 15 is a view illustrating the brake according to the other embodiment when the coupling is in a normal state.

Referring to FIG. 15, when the coupling 73 according to the other embodiment is in a normal state, one side of the stopper 83 of the brake 8 is inserted into the stopper receiver 811 provided in the top holder 81, and the other side of the stopper 83 is seated in the stopper seat 822 provided for the bottom holder 82. The elastic member 84 received in the stopper receiver 811 may press the stopper 83 toward the bottom holder 82.

The driving force of the motor 72 may be transmitted to the ball screw 70 via the drive shaft 720 and the coupling 73. The ball screw 70 connected to the side of the top holder 81 may rotate at the same speed and in the same rotational direction as the drive shaft 720 connected to the bottom holder 82.

That is, when the coupling 73 is in the normal state, the stopper 83 received in the stopper receiver 811 may rotate at the same speed and in the same rotational direction as the drive shaft 720 without interfering with the bottom holder 82. The main body 7 may be raised or lowered depending on the rotational direction of the ball screw 70. As an example, when the drive shaft 720 and the ball screw 70 are rotated in the clockwise direction A, the main body 7 may be raised. When the drive shaft 720 and the ball screw 70 are rotated in the counterclockwise direction B, the main body 7 may be lowered.

When the coupling 73 is ruptured, the rotational speed and direction of the side of the top holder 81 may be different from those of the side of the bottom holder 82. Hereinafter, a structure in which the rotation of the ball screw 70 is stopped by the brake 8 will be described.

Figure 16:
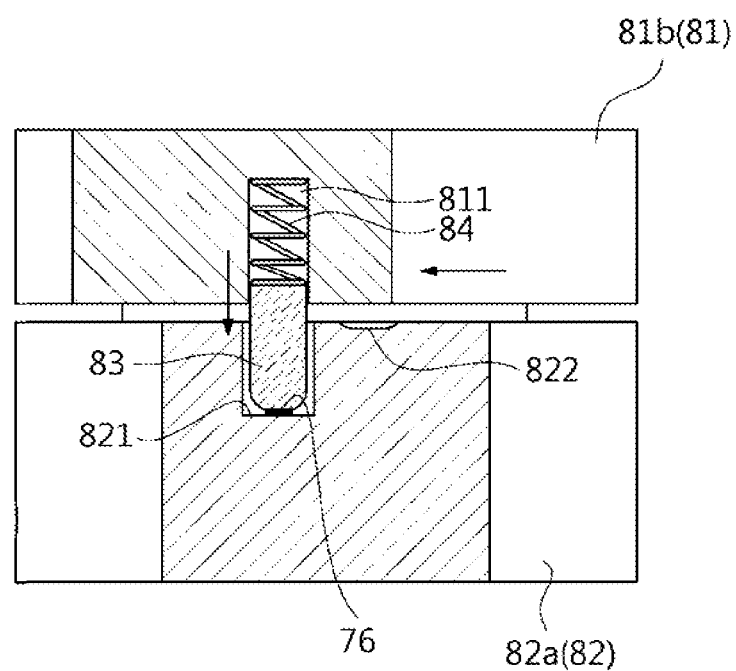
FIG. 16 is a view illustrating the brake according to the other embodiment when the coupling is damaged.

FIG. 16 is a view illustrating the brake according to the other embodiment when the coupling is damaged.

Referring to FIG. 16, when the coupling 73 according to the other embodiment is ruptured into an upper coupling 73a and a lower coupling 73b, a difference in rotational direction or speed between the ball screw 70 connected to the upper coupling 73a and the drive shaft 720 connected to the lower coupling 73b may occur.

When the coupling 73 is ruptured while the main body 7 is raised by the rotation of the drive shaft 720 and the ball screw 70 in the clockwise direction A, the side of the upper coupling 73a and the side of the lower coupling 73b may be rotated in different directions. The drive shaft 720 connected to the side of the lower coupling 73b continues to be rotated in the clockwise direction A by the driving force of the motor 72, while the rotating force of the drive shaft 720 may not be transmitted to the ball screw 70 connected to the side of the upper coupling 73a. The ball screw 70 may be rotated in a direction in which the main body 7 attempts to move downward by its own weight, that is, in the counterclockwise direction B.

Accordingly, the upper coupling 73a to which the ball screw 70 is connected may be rotated in the counterclockwise direction B, and the lower coupling 73b to which the drive shaft 720 is connected may be rotated in the clockwise direction A. The top holder 81 provided at the side of the upper coupling 73a may be rotated in the counterclockwise direction B, and the bottom holder 82 provided at the side of the lower coupling 73b may be rotated in the clockwise direction A.

As the rotational directions of the upper coupling 73a and the lower coupling 73b are different from each other, the stopper 83 is rotated together with the top holder 81, and can come out of the stopper seat 822 of the bottom holder 82. The stopper 83 coming out of the stopper seat 822 may slide on the upper surface of the bottom holder 82, and be inserted into the interfering hole 821 when the stopper 83 arrives at the interfering hole 821. The stopper 83 may be inserted into the interfering hole 821 by an elastic force of the elastic member 84.

An upper side of the stopper 83 may be partly received into the stopper receiver 811 provided at the side of the top holder 81, and a lower side of the stopper 83 may be partly received into the interfering hole 821 provided at the side of the bottom holder 82. The upper coupling 73a connected to the side of the top holder 81 and the lower coupling 73b connected to the side of the bottom holder 82 may be rotated at the same rotational speed in the clockwise direction A by the stopper 83 that restrains the top holder 81 and the bottom holder 82. Accordingly, the rotating force of the drive shaft 720 may be transmitted to the ball screw 70.

A switch 76 may be provided at one side of the interfering hole 821 of the bottom holder 82. When the stopper 83 is inserted into the interfering hole 821, the switch 76 may be pressed. When the switch 76 is pressed, a signal indicating that the coupling 73 is ruptured may be sent to the controller (not shown). The controller that has received the signal may stop the operation of the mammography apparatus 5.

When the coupling 73 is ruptured while the main body 7 is lowered by the rotation of the drive shaft 720 and the ball screw 70 in the counterclockwise direction B, the rotational speed of the upper coupling 73a may be different from that of the lower coupling 73b. The ball screw 70 may receive a force in a direction in which the main body 7 attempts to move downward due to its own weight, and thus be rotated faster than the rotational speed of the drive shaft 720 in the counterclockwise direction B. Accordingly, the upper coupling 73a to which the ball screw 70 is connected may be rotated at a faster speed than the lower coupling 73b to which the drive shaft 720 is connected.

As the top holder 81 provided at the side of the upper coupling 73a may be rotated at a faster speed than the bottom bolder 82 provided at the side of the lower coupling 73b in the counterclockwise direction B, the stopper 83 provided at the side of the top holder 81 may come out of the stopper seat 822 of the bottom holder 82 and then move along the upper surface of the bottom holder 82. When the stopper 83 reaches the interfering groove 821, the stopper 83 may be inserted into the interfering hole 821 by the elastic member 84.

The upper side of the stopper 83 may be partly received into the stopper receiver 811 of the top holder 81, and the lower side of the bottom 82 may be partly received into the interfering hole 821 of the bottom holder 82. The upper coupling 73a connected to the side of the top holder 81 and the lower coupling 73b connected to the side of the bottom holder 82 may be rotated at the same rotational speed in the counterclockwise direction B by the stopper 83 that restrains the top holder 81 and the bottom holder 82. Accordingly, the rotating force of the drive shaft 720 may be transmitted to the ball screw 70.

When the stopper 83 is inserted into the interfering portion 821, the switch 76 provided in the interfering hole 821 is pressed, and when the switch 76 is pressed, a signal indicating that the coupling 73 is ruptured may be sent to the controller. The controller, which has received the signal indicating that the coupling 73 is ruptured, may stop the operation of the mammography apparatus 5.

The mammography apparatus may also include an embodiment with a lifting arm to which a main body is connected and which is movable up and down. A motor may be configured to transmit a movement force to the lifting arm with a coupling, at one side of which the lifting arm is connected and at the other side of which a drive shaft of the motor is connected. A brake may be provided at one side of the coupling. The brake may include a top holder provided at one side of the coupling and having a stopper, and a bottom holder provided at an other side of the coupling. As a result, when the coupling is ruptured, a stopper interferes with an interfering portion to prevent the one side of the coupling from being rotated separately from the other side of the coupling. An interfering bracket may be provided at one side of the coupling, and the stopper interferes with the interfering bracket and when the interfering bracket interferes with the stopper, the main body stops moving up and down. A stopper receiver may be configured to receive the stopper and may be provided for the bottom holder. When a part of the stopper is inserted into the stopper receiver, the top holder and the bottom holder are mutually restrained and rotated together and when the stopper is inserted into the stopper receiver, a driving force of the motor is transmitted to the lifting arm. The brake may be a mechanical brake.

The mammography apparatus may also include an embodiment with a main body having an x-ray generator and an x-ray detector and an arm connected to the main body. A screw may be used to position the arm with a coupling to engage the screw and a motor to drive the coupling. A rotation lock stop mechanism may be associated with the coupling to stop the screw when the coupling breaks and the screw tries to rotate to drop the arm downward.

In this way, the brake having the mechanical structure is provided. Thereby, even when the coupling is ruptured, a fall of the main body can be reliably prevented. In addition, the brake having the mechanical structure is manufactured at a lower cost than the electronic brake. The brake accordingly the present embodiments may be easily applied to not only the mammography apparatus, but also other apparatuses having a similar lifting structure.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A mammography apparatus, comprising:
a main body having an X-ray generator and an X-ray detector;
a lifting arm to which the main body is connected;
a motor configured to generate a driving force for the lifting arm;
a coupling configured to transfer the driving force from the motor to the lifting arm, at one side of which a drive shaft provided for the motor is connected, and at an other side of which the lifting arm is connected;
a holder provided at the one side of the coupling to be rotatable together with the coupling; and
a stopper provided for the holder and protruded from the holder to interfere with an interfering portion to obstruct rotation of the one side of the coupling when the coupling is ruptured.

2. The mammography apparatus of claim 1, wherein the holder includes a top holder located at an upper portion of the coupling, and a bottom holder located at a lower portion of the coupling.

3. The mammography apparatus of claim 2, wherein the stopper is provided for the top holder, and the bottom holder is provided with a push bar pressing the stopper when the coupling is ruptured.

4. The mammography apparatus of claim 3, wherein when the stopper is pressed by the push bar, the stopper protrudes from one side of the top holder.

5. The mammography apparatus of claim 4, wherein an interfering portion is located at the one side of the coupling, the interfering portion interfering with the stopper protruding from the one side of the top holder.

6. The mammography apparatus of claim 5, wherein, when the stopper is interfered with by the interfering portion, the lifting arm is stopped.

7. The mammography apparatus of claim 5, wherein the interfering portion includes a switch pressed by the stopper.

8. The mammography apparatus of claim 7, wherein, when the switch is pressed, a signal indicating that the coupling is ruptured is sent to a controller.

9. The mammography apparatus of claim 3, wherein the top holder further includes an elastic member, and the elastic member presses the stopper toward a push bar side.

10. The mammography apparatus of claim 9, wherein an elastic member receiver configured to receive the elastic member is provided in an inner portion of the stopper.

11. The mammography apparatus of claim 3, wherein a stopper receiver is provided at one side of the top holder.

12. The mammography apparatus of claim 11, wherein a lateral hole is formed in the top holder, and the stopper is configured to protrude through the lateral hole.

13. The mammography apparatus of claim 12, wherein a pin is located in the lateral hole to cross the lateral hole.

14. The mammography apparatus of claim 13, wherein the stopper includes a first surface and a second surface that are spaced apart from each other, and when the stopper is pressed by the push bar, the pin is positioned between the first surface and the second surface.

15. The mammography apparatus of claim 1, wherein the lifting arm comprises a ball screw.

16. A mammography apparatus, comprising:
a main body having an X-ray generator and an X-ray detector;
a lifting arm to which the main body is connected to be movable up and down;
a coupling configured to transfer a driving force from a motor to the lifting arm, at one side of which the lifting arm is connected and at an other side of which a drive shaft connected to the motor is connected; and
a brake configured to prevent ruptured coupling portions from being separately rotated when the coupling is ruptured,
wherein the brake includes:
　a top holder provided at one side of the coupling;
　a bottom holder provided at an other side of the coupling; and
　a stopper configured to restrain the top holder and the bottom holder when the coupling is ruptured such that the lifting arm and the drive shaft are moved together.

17. The mammography apparatus of claim 16, wherein a stopper receiver configured to receive the stopper is provided at one side of the top holder.

18. The mammography apparatus of claim 17, wherein when the coupling is in a normal state, one side of the stopper is supported by one side of the bottom holder.

19. The mammography apparatus of claim 17, wherein an interfering hole, into which a part of the stopper is inserted when the coupling is ruptured, is provided at one side of the bottom holder.

20. The mammography apparatus of claim 17, wherein an elastic member is further provided for the stopper receiver.

21. The mammography apparatus of claim 20, wherein the elastic member presses the stopper toward the bottom holder.

22. An apparatus, comprising:
a main body having an x-ray generator and an x-ray detector;
an lifting arm connected to the main body;
a ball nut mounted to the lifting arm to move up or down along the lifting arm;
a coupling configured to engage the lifting arm and configured to transfer the driving force from motor to the lifting arm; and
a stop mechanism including a stopper interfering with an interfering portion by protruding to stop the lifting arm from changing position if the coupling breaks.

23. The apparatus of claim 22, wherein the apparatus is a mammography apparatus, the coupling comprises first and second parts and the stop mechanism comprises:
a bracket associated with the coupling;
a push bar of the second part; and
a stop rod of the second part pushed by the push bar when the first part rotates differently than the second part where the stop rod is pushed out to be in contact with the bracket to stop rotation of the second part.

24. The apparatus of claim 22, further comprising a switch, activated by the stop rod when pushed out, to signal a broken coupling.

25. A mammography apparatus, comprising:
a main body having an x-ray generator and an x-ray detector;
an arm connected to the main body;
a linear actuator configured to generate a driving force for the arm and to position the arm; and
a stop mechanism including a stopper protruded from the linear actuator to engage the linear actuator to stop the arm from changing position if the actuator breaks.

26. The apparatus of claim 25, wherein the linear actuator comprises a mechanical linear actuator and the stop mechanism comprises a mechanical brake including an extensible pin on an arm lifting shaft that contacts a rigid bracket to stop shaft rotation.

* * * * *